United States Patent [19]

Joyashiki et al.

[11] Patent Number: 4,710,995
[45] Date of Patent: Dec. 8, 1987

[54] ELECTRIC MOTOR DRIVEN TOOTHBRUSH

[75] Inventors: Hisashi Joyashiki, Takatsuki; Minoru Iwasawa, Moriyama; Masakazu Oohigashi, Yao; Masao Terai, Kobe, all of Japan

[73] Assignee: Sunstar Kabushiki Kaisha, Osaka, Japan

[21] Appl. No.: 841,325

[22] Filed: Mar. 19, 1986

[30] Foreign Application Priority Data

Mar. 19, 1985 [JP] Japan .................................. 60-56347
Mar. 19, 1985 [JP] Japan .................................. 60-40768[U]
Mar. 19, 1985 [JP] Japan .................................. 60-40769[U]
Jan. 31, 1986 [JP] Japan .................................. 61-13447[U]

[51] Int. Cl.$^4$ ............................................ A46B 13/02
[52] U.S. Cl. ................................................ 15/22 R
[58] Field of Search .................. 15/22 R, 22 A, 22 C

[56] References Cited

U.S. PATENT DOCUMENTS 3,489,936  1/1970  Boyles .................................. 15/22 R
3,546,501 12/1970  Kircher ................................ 15/22 R

FOREIGN PATENT DOCUMENTS

0004358  1/1977  Japan .................................. 15/22 R

Primary Examiner—Edward L. Roberts
Attorney, Agent, or Firm—Wegner & Bretschneider

[57] ABSTRACT

The present invention is directed to a motor driven toothbrush, having a scrubbing shaft supported on a standard secured to an end plate of a housing and movable in a direction of the axis of the scrubbing shaft, a rolling shaft coaxially fitted to the scrubbing shaft and movable around the axis of the rolling shaft, first drive means driven by an electric motor for driving said scrubbing shaft reciprocally in the axial direction, second drive means driven by the rotation of the electric motor for swinging said rolling shaft reciprocally around the axis of the rolling shaft, and adapter means having a toothbrush unit and being detachably mounted to the rolling shaft and/or the scrubbing shaft, whereby the operator of the toothbrush can select the scrubbing motion or rolling motion of the toothbrush as desired.

8 Claims, 30 Drawing Figures

ELECTRIC MOTOR DRIVEN TOOTHBRUSH

BACKGROUND OF THE INVENTION

1. Field of the Invention

The present invention relates to a toothbrush, and more particularly to a toothbrush driven by an electric motor in either a rolling motion and a scrubbing motion.

2. Description of the Prior Art

Known motor driven toothbrushes can exclusively act in only one mode, either providing rolling motion in which the brush rotates around the axis of the shaft V or oscillatory or a scrubbing motion in which the brush moves in a direction of the axis of the shaft.

There are known various ways of toothbrushing, for example, a way of using brush ends, a way of using intermediate portion of each filament of a brush, a lateral brushing in which a toothbrush is moved laterally or horizontally, a vertical brushing in which a toothbrush is moved in the longitudinal direction of teeth and a rolling brushing in which a tooth brush is rotated in the vertical direction.

It is considered that a combination of various ways of brushing as mentioned above is more valuable to obtain the effect of toothbrushing rather than limiting it exclusively to one way of brushing.

SUMMARY OF THE INVENTION

An essential object of the present invention is to provide an improved toothbrush which is able to perform either the rolling motion or scrubbing motion of the tooth brush as desired.

According to the present invention, there is provided a motor driven toothbrush comprising a housing having an end plate formed on one end portion of the housing, an electric motor accommodated in the housing with the motor shaft projected outward of the housing through the end plate, a scrubbing shaft supported on a standard secured to the end plate of the housing for moving in a direction of the axis of the scrubbing shaft, a rolling shaft coaxially fitted to the scrubbing shaft for moving around the axis of the rolling shaft, first drive means driven by the rotation of the electric motor for driving said scrubbing shaft reciprocally in the axial direction, second drive means driven by the rotation of the electric motor for swinging said rolling shaft reciprocally around the axis of the rolling shaft, and adapter means having a toothbrush unit and being detachably mounted to the rolling shaft and/or the scrubbing shaft.

DETAILED DESCRIPTION OF THE PREFERRED EMBODIMENTS

Figure 1:
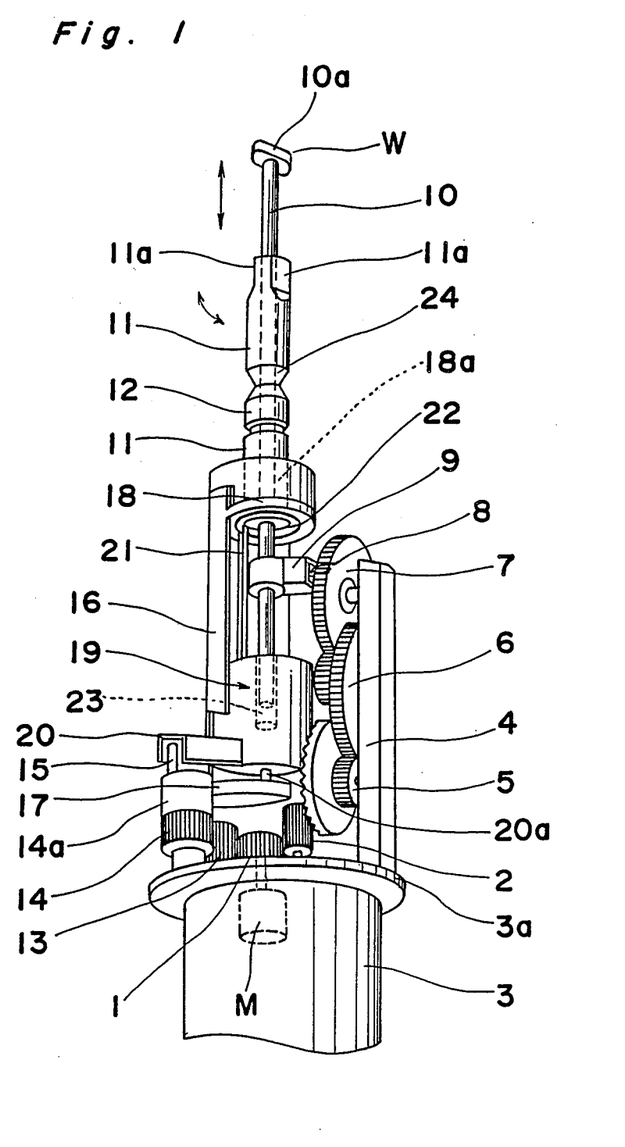
FIG. 1 is a perspective view of an embodiment of a toothbrush according to the present invention.
Figure 2:
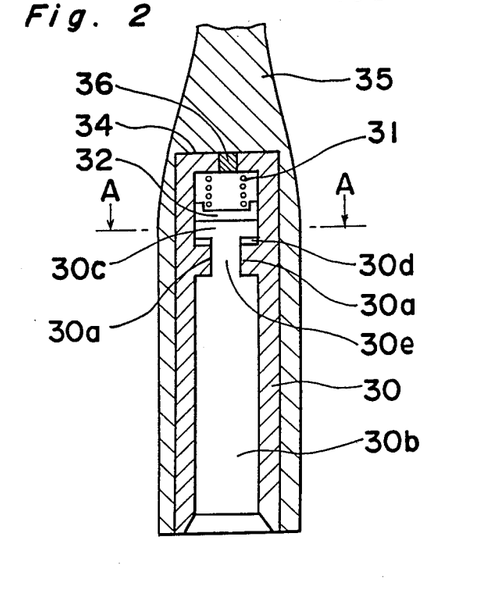
FIG. 2 is a cross sectional view of an adapter used for the toothbrush according to the present invention.
Figure 3:
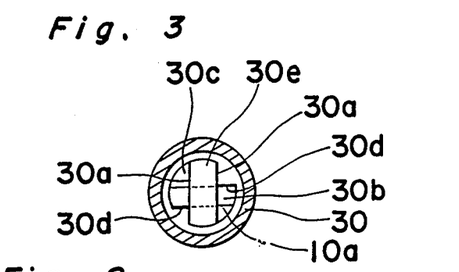
FIG. 3 is a cross sectional view taken along the line A—A in FIG. 2.
Figure 4:
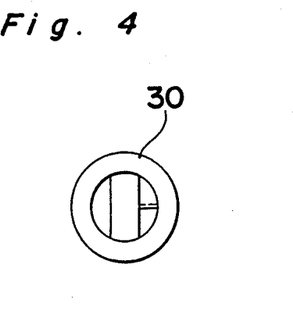
FIG. 4 is a bottom view of the adapter shown in FIG. 2.
Figure 5:
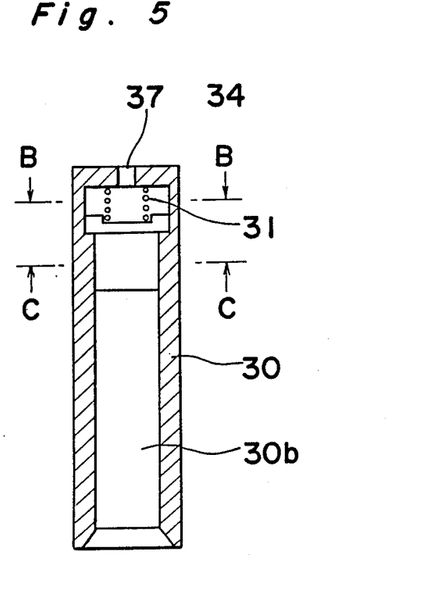
FIG. 5 is a cross sectional view of another example of adapter for use in the toothbrush according to the present invention.
Figure 6:
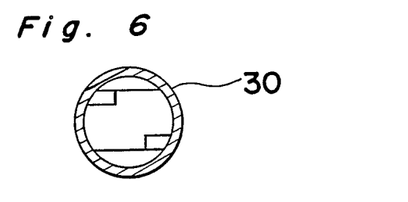
FIG. 6 is a cross sectional view taken along the line B—B in FIG. 5.
Figure 7:
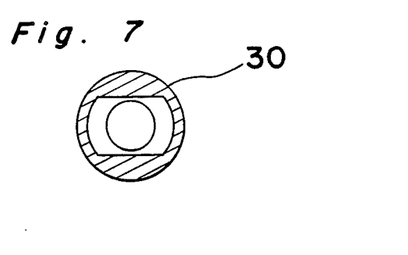
FIG. 7 is a cross sectional view taken along the line C—C in FIG. 5.
Figure 8:
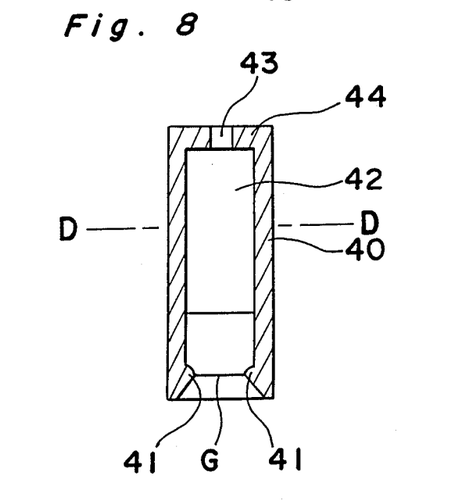
FIG. 8 is a cross sectional view of a further example of the adapter.
Figure 9:
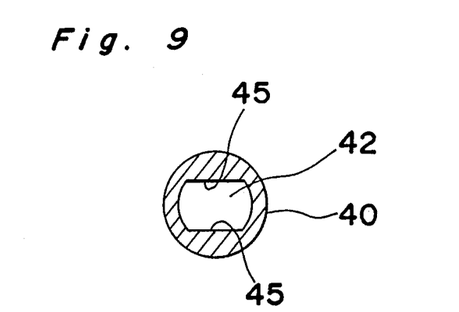
FIG. 9 is a cross-sectional view taken along the line D—D of the adapter shown in FIG. 8.
Figure 10:
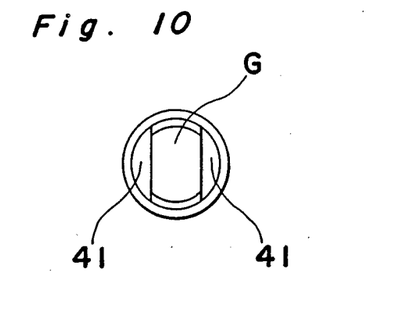
FIG. 10 is a bottom plan view of the adapter shown in FIG. 8.
Figure 11:
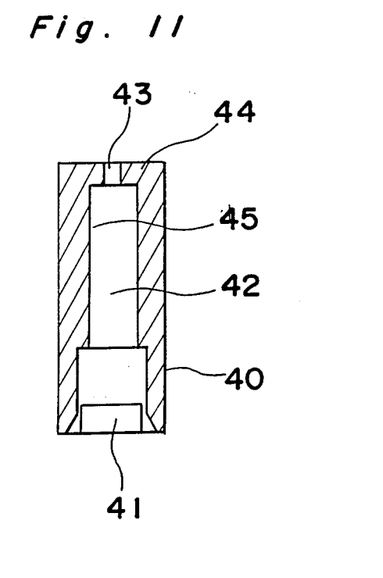
FIG. 11 is a cross sectional view of a still further example of the adapter.

Referring to FIG. 1, a small sized electric motor M is accommodated in a cylindrical chamber of a housing 3 of a handle portion of a toothbrush according to the present invention. A motor gear 1 mounted to the rotation shaft of the motor M is coupled to a scrubbing drive gear 2 which is rotatably supported on an end plate 3a of the housing 3. A crown gear 5, an intermediate gear 6 and a main scrubbing gear 7 are respectively rotatably supported on a standard 4 fixed on the end plate 3a so that the respective gears 5, 6 and 7 are so mounted that they are coupled together and rotate in the respective vertical planes. A crank member 9 integrally secured to a scrubbing shaft 10 slidably supported by a cylindrical outer bearing member 18 is coupled to a crank pin 8 projected from a position eccentric to the center of the gear of the scrubbing gear 7 so that, upon rotation of the scrubbing gear 7, the scrubbing crank member 9 and the scrubbing shaft 10 can be moved in a direction of the axis of the scrubbing shaft 10 by the crank motion of the scrubbing gear 7. A second standard 16 is secured to the end plate 3a of the housing 3 and said outer bearing member 18 is formed on one end of the second standard. Said scrubbing shaft 10 is axially slidably penetrated through a through hole 12 defined centrally in a rolling shaft 11.

A rolling drive gear 13 is rotatably supported on the end plate 3a of the housing, having the gear coupled with the motor gear 1. A rolling gear 14 is rotatably supported on the end plate 3a and is coupled to the rolling drive gear 13. A roller 14a is integrally coupled with the rolling gear 14 and a crank pin 15 is projected on the end face of the roller 14a eccentric from the center of the roller 14a. Said crank pin 15 is coupled to a crank lever 20 projected radially from the cylindrical surface of a rolling crank 19 of a cylindrical shape having its center shaft 20a rotatably supported on a supporting plate 17 secured to the second standard 16.

A crank transfer shaft 21 is projected from the top end of the rolling crank 19 and the top end of the crank transfer shaft 21 is securely connected to a cylindrical inner bearing member 22 rotatably coaxially fitted in a through hole 18a of the bearing member 18. The inner bearing member 22 projects beyond the top face of the bearing member 18 so as to form the lower part of the rolling shaft 11.

The lower end portion of the scrubbing shaft 10 is slidably fitted in a supporting hole 23 in the central portion of the rolling crank 19.

The rolling shaft 11 is provided with an engaging cut portion 24 with a bevelled shape so as to detachably engage with a toothbrush adapter which will be described later.

The top end portion of the scrubbing shaft 10 is provided with a tip 10a in the form of a generally T-shaped small plate for coupling with said adapter. The top end portion of the rolling shaft 11 is shaped to provide an opposite flat surfaces 11a for engagement with the adapter.

Referring to FIGS. 2 to 7, the scrubbing adapter 30 has a cylindrical shape with the inner cylindrical surface formed so as to be slidably fitted onto the rolling shaft 11. The axially inner portion 30b of the adapter 30 is provided with a pair of engaging members 30a radially inwardly projected from the inner cylindrical surface of the adapter so as to define a gap 30e through which the tip 10a can pass in case the small width part w of the tip 10a passes gap 30a. On the top surface of each of the projections 30a, a recess 30c is formed so that when the adapter is fitted to the scrubbing shaft 11 the tip 10a can fit in the recess 30c as shown in the chain lines in FIG. 3, thereby the adapter 30 can be detachable connected with the scrubbing shaft 10. In this case, the shoulders 30d constrain the tip 10 for preventing rotation of the tip 10a. In order to press the top face of the tip 10a when the tip is inserted, there is provided a pressing plate 32 biased toward the projection 30a by a spring 31. A hole 37 is defined on the top plate 34 of the adapter 30 so that when a brush unit 35 is fitted to the adapter 30, a projection 36 of the brush unit 35 can be inserted in the hole 37 to assure connection of the adapter 30 and the brush unit 35.

Referring to FIGS. 8 to 11, a rolling adapter 40 has cylindrical shape having an elongated cavity 42 of an oval shape in cross section and a pair of engaging projections 41 inwardly projected having their free ends opposed defining a gap G. In this arrangement, when the adapter 40 is fitted to the rolling shaft 11, the flat surfaces 11a can engage with the parallel flat wall 45 and the projection 41 can fit with the engaging recess 24 so that the adapter is prevented from being disengaged from the rolling shaft 11. It is noted that the cavity 42 should be long enough to accommodate therein the scrubbing shaft 10. An opening 43 for the same purpose of the opening 37 is also defined on the top plate 44. Said adapter 40 is also fitted to the brush unit 35 similar to the manner shown in FIG. 2.

Figure 12:
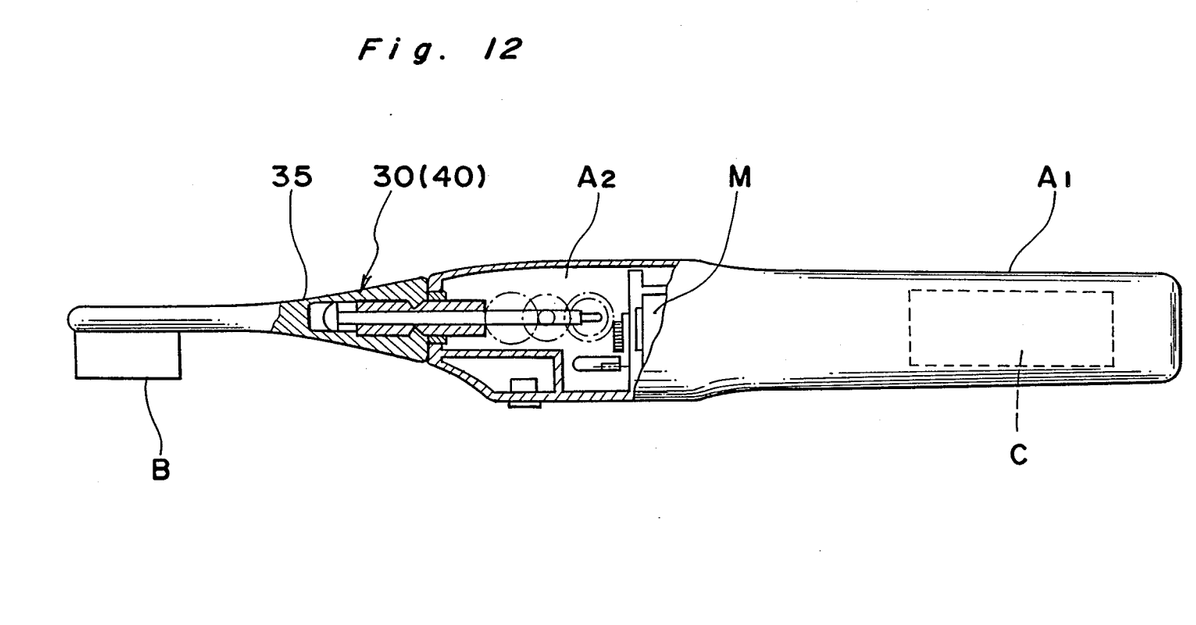
FIG. 12 is a general side view of the toothbrush shown in FIG. 1 with partly broken.

Referring to FIG. 12 showing an entire toothbrush according to the present invention in which a housing 3 is contained in a handle portion A1 and the drive arrangement shown in FIG. 1 is contained in a driving chamber A2 connected to the handle portion A1 and the brush unit 35 with the adapter 30 or 40 and a brush B.

In operation, in case of mounting the scrubbing adapter 30 to the toothbrush arrangement shown in FIG. 1, the scrubbing shaft 10 with the rolling shaft 11 is inserted in the hole 30h of the adapter 30 and the engaging chip 10a is entered into the space 30s above the projections 30a through the gap 30b. By rotating the adapter 30 about 90° as shown in the dotted line in FIG. 3, so that the engaging chip 10a is clamped between the projections 30a and pressing plate 32. Thus the adapter 30 can be mounted to the toothbrush arrangement. When the motor M is driven by a battery accommodated in the housing 3, rotation of the motor gear 1 is transferred to the scrubbing gear 7, which can be rotated. Rotation of the scrubbing gear 7 causes the scrubbing crank 9 and the scrubbing shaft 10 to be reciprocally moved in the axis of the scrubbing shaft 10 by the crank motion of the crank pin 8 and the scrubbing crank 9. Although the rolling crank 19 is reciprocally rotated by the rotation of the rolling gear 14 and the crank action of the pin 15 and the crank lever 20, since the adapter 30 is not engaged with the rolling shaft 11 because of the clearance between the inner cylindrical face of the adapter 30 and the rolling shaft 11, the adapter 30 does not rotate.

By the movement of the adapter 30 in the axis of the scrubbing shaft 10, the brush B also reciprocally moved in the direction of the axis of the scrubbing shaft 10 so that the man using the toothbrush can brush his teeth in a scrubbing manner.

In case the adapter 40 is mounted to the toothbrush arrangement shown in FIG. 1, in place of the adapter 30, the projections 41 can be engaged in the engaging recess 24 and the flat walls 45 of the adapter 30 engages with the flat surfaces 11a of the rolling shaft 11. In this case, although the scrubbing shaft 10 is present in the cavity 42, the scrubbing shaft 10 does not engage with any parts of the adapter. When the motor M is rotated the scrubbing crank 19 swing reciprocally around the axis of the crank 19, The swing motion of the scrubbing crank 19 is transferred to the bearing 22 and the scrubbing shaft 11 is reciprocally rotated, so that the brush b can also be reciprocally rotated around the axis of the rolling shaft 11, then the man can brush his teeth in the rolling manner.

Figure 13:
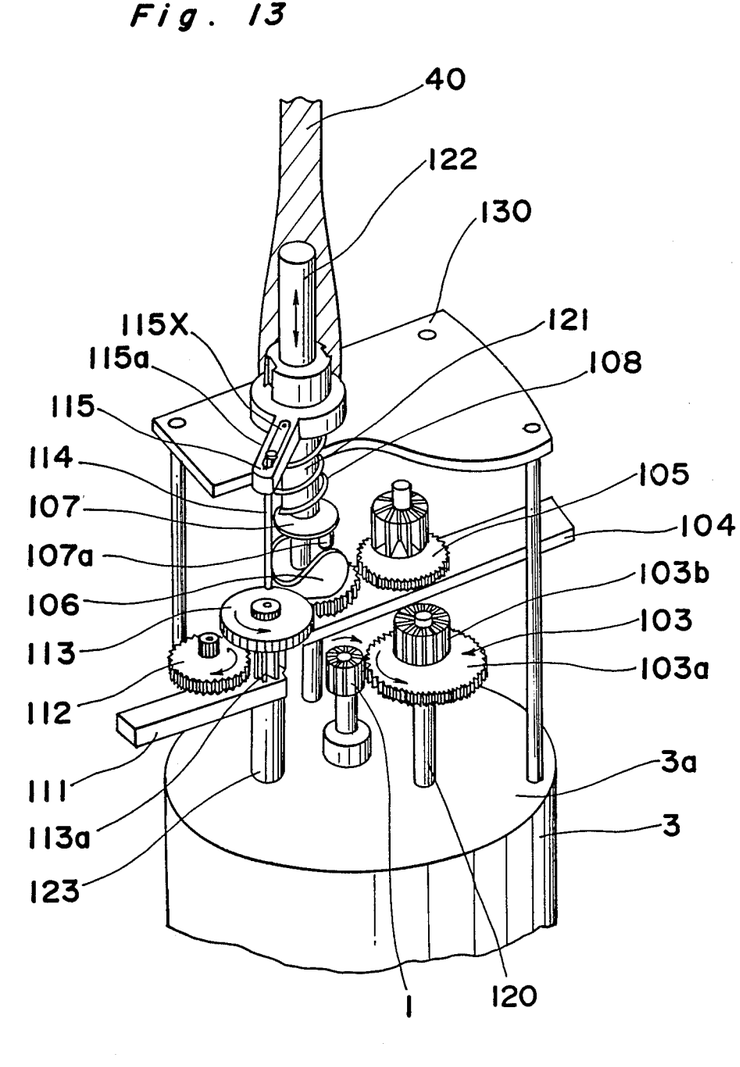
FIG. 13 is a perspective view of an essential portion of another embodiment of the toothbrush according to the present invention.

FIG. 13 shows a second embodiment of the toothbrush according to the present invention in which an intermediate gear arrangement 103 having a large gear 103a and a small gear 103b is rotatably supported on the top plate 3a by a shaft 120 so that the large gear 103a engages with the motor gear 1. A scrubbing change over lever 104 is rotatably supported on another shaft 121 and a cylindrical scrubbing cam 106 with a gear 106a is rotatably mounted on the scrubbing change over lever 104. The top end face of the cylinder of the scrubbing cam 106 is curved in the form of a smooth wave. A scrubbing gear 105 is rotatably mounted on the scrubbing change over lever 104 so that the gear 105 engages with the gear 106a. A supporting shaft 122 is supported on a frame plate 130 rotatably and slidably in connection with the axis of the supporting shaft 122 and a cam follower plate 107 having a cam follower pin 107a is attached to the bottom end of the supporting shaft 122. The cam follower plate 107 is normally biased toward the scrubbing cam 106 by means of a spring 108. The cam follower pin 107a is slidably contacted with the top end surface of the srubbing cam 106, so that, when the scrubbing cam 106 is rotated, as the contact point of the cam follower pin 107a with the scrubbing cam 106 moves from the peak to the bottom of the cam 106, the supporting shaft 122 moves toward the cam 106. As the contact point moves from the bottom to peak of the cam follower 106, the supporting shaft 122 moves in the direction away from the scrubbing cam 106. In this way the supporting shaft 122 can reciprocally move in the direction of the axis of the supporting shaft 122.

A rolling change over lever 111 is rotatably supported on the supporting rod 123 and a rolling change over gear 112 and rolling gear 113 are rotatably supported on the lever 111. Both of the gears 112 and 113 are coupled by an intermediate gear 113a. The rolling change over gear 112 is set in the same level as the level of the intermediate gear 103b, so that when the lever 111 is moved to the intermediate gear 103, the rolling change over gear 112 can engage with the intermediate gear 103b.

A rolling actuating member 115 is mounted to the supporting shaft 122, with an arm 115a radially projecting therefrom An end of a rolling shaft 114, projected from the eccentric position of the rolling gear 113, is adapted to be slidably engaged in an elongated opening 115x defined in the arm 115a. When the rolling gear 113 is rotated, the rolling actuation member 115 can be reciprocally rotated around the axis of the supporting shaft 122.

In the second embodiment of the toothbrush as mentioned above, when the scrubbing lever 104 is manually rotated toward the intermediate gear arrangement 103 and the scrubbing gear 105 engages with the small gear 103b, the rotation of the motor gear 1 is transferred to the gear 106a and the scrubbing cam 106 is rotated and the supporting shaft 122 is reciprocally moved in the direction of the axis of the supporting shaft 122. Therefore, when an adapter 140 is used similar to adapter 40 mentioned in the first embodiment, the brush can be moved in the scrubbing manner.

If, the rolling change over lever 111 is moved toward the intermediate gear arrangment 103, the rolling change over gear 112 engages with the small gear 103b and the rotation of the motor gear 1 is transferred to the rolling gear 113. This causes the rolling lever 115 to be reciprocally rotated and the supporting shaft 122 and the brush are moved in the rolling manner. If the scrubbing change over gear 105 and the rolling change over gear 112 both engages the intermediate gear arrangement, the supporting shaft 122 and the brush can be moved in both a scrubbing manner and a rolling manner simultaneously.

In the second embodiment, the arrangement shown in FIG. 13 is covered by a suitable cylindrical case (not shown) and the scrubbing change over lever 104 and the rolling change over lever 111 may project outside of the case so as to manually operate both levers.

Figure 14A:
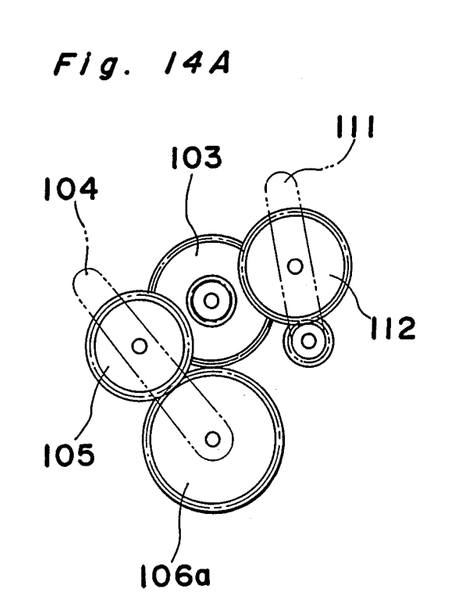
FIG. 14A to 14C are respectively top plan views showing operation of the gear arrangement used in the toothbrush shown in FIG. 13.
Figure 14B:
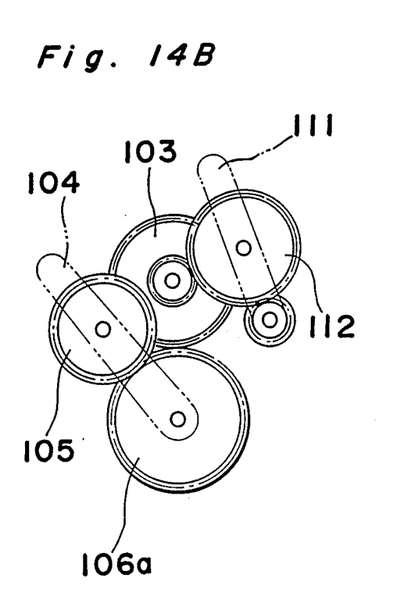
Figure 14C:
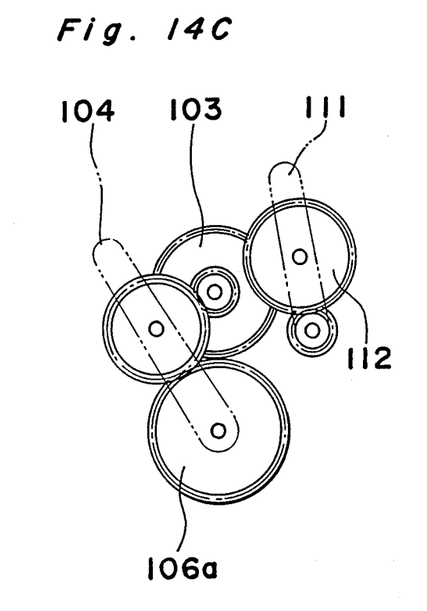
Figure 15:
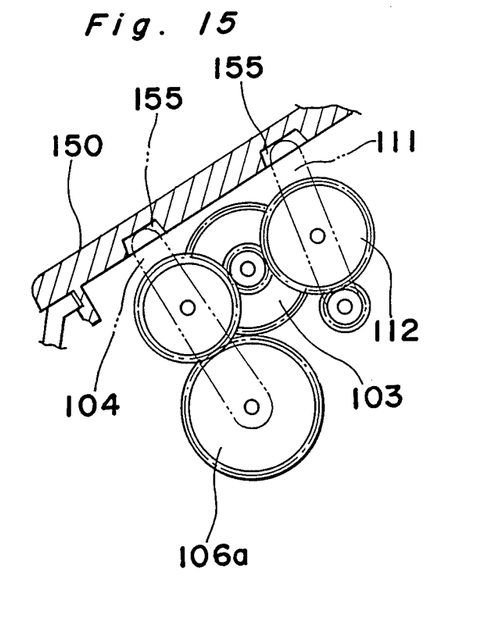
FIG. 15 is a top plan view of the gear arragnement shown in FIG. 13 with an operation member shown.
Figure 16:
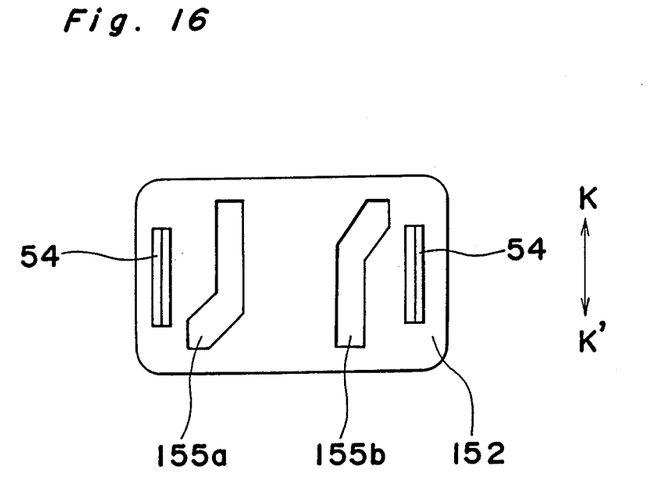
FIG. 16 is a front view of the operation member shown in FIG. 15.
Figure 17:
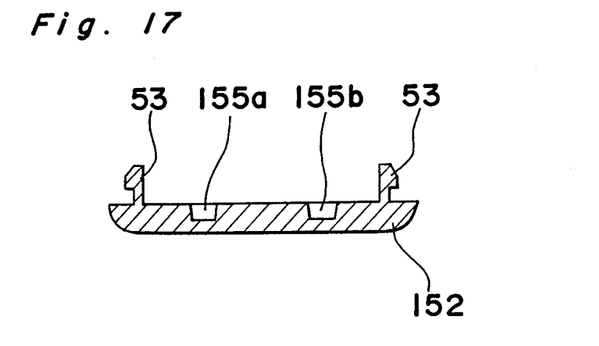
FIG. 17 is a cross sectional view of the operation member shown in FIG. 16.

The scrubbing change over lever 104, rolling change over lever 111 and the respective gears 105, 112 and 113 may be disposed in such a manner as shown in FIGS. 14A to 14C with an operation button 150 engaged with the free ends of the respective levers 104 and 111 as shown in FIG. 15. The operation button 150 is formed of a movable plate 152 and a pair of legs 153 of the movable plate 152 is movably engaged with a part of the casing 3. The free ends of the levers 104 and 111 are respectively movably engaged in the recesses 155a and 155b. When the movable plate 152 is moved in a direction K in FIG. 16, one of the levers 104 and 111 can be moved guided by the bent portion of the recess 155a and the lever 104 can be changed over. In case the button is moved in the direction K', the lever 111 can be rotated guided by the bent portion of the recess 155b and the lever 111 can be changed over.

Figure 18:
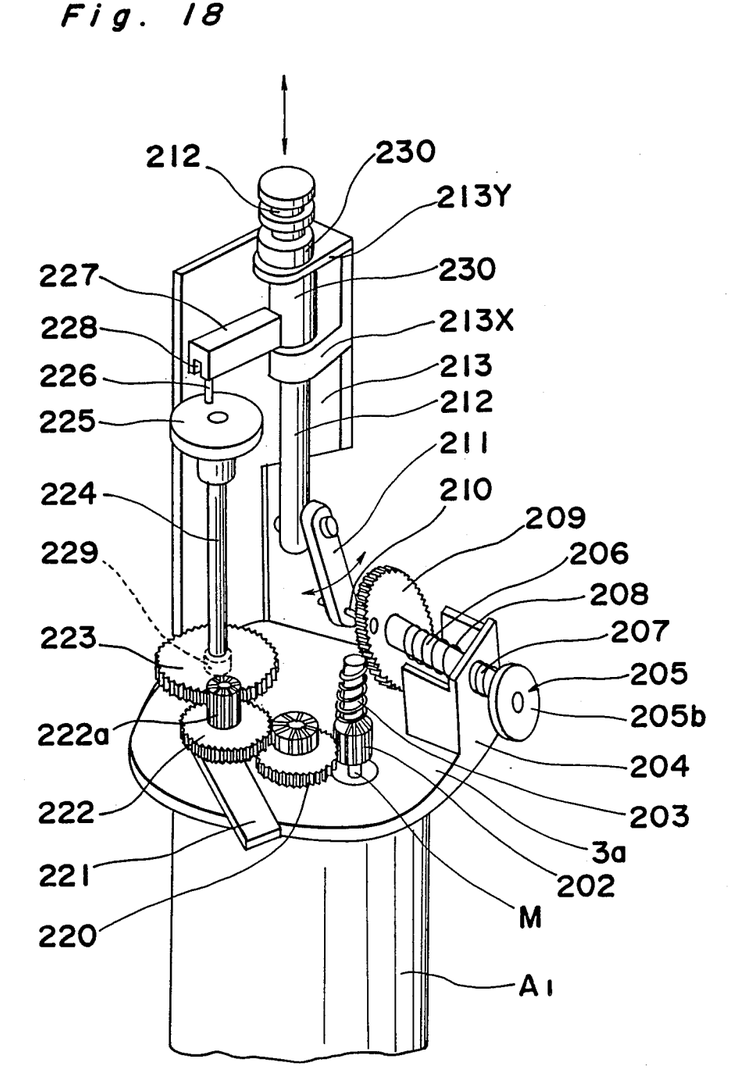
FIG. 18 is a perspective view of an essential portion of a further embodiment of the toothbrush according to the present invention.

Referring to FIG. 18 showing a third embodiment of the toothbrush according to the present invention in which a rolling drive gear 202 and scrubbing drive gear 203 are respectively attached to the motor shaft M1 of the motor M. A scrubbing switch 205 is manually operably mounted on a bracket 204 provided on the top plate 3a. Said scrubbing switch 205 comprises an operation shaft 206 attached to the bracket 204 so as to reciprocally move in a direction of the axis of the shaft 206, a knob 205b attached to one end of the shaft 206 and a scrubbing gear 209 attached to the other end of the shaft 206. The shaft 206 is normally biassed in a right direction on the drawings by a spring 207 disposed between the bracket 204 and the knob 205b so that the scrubbing gear 209 is normally away from the scrubbing drive gear 203. A crank pin 210 is projected from the end face of the scrubbing gear 209 at a position eccentric from the center of the scrubbing gear 209 and the crank pin 210 is coupled to a lower end portion of a crank lever 211 the upper end portion of which is coupled to a lower end of a scrubbing shaft 212 which is supported on a arm 213x of a standard 213 projected from the top plate 3a. By this arrangement the scrubbing shaft 212 can be reciprocally moved in the direction of the axis of the scrubbing shaft 212 by the crank motion of the arrangement of the scrubbing gear 209, crank pin 210, crank lever 211 and the scrubbing shaft 212 when the gear 209 is rotated.

The scrubbing shaft 212 is adapted to movably penetrate a top end plate 213Y of the standard 213 for engagement of a toothbrush unit. An intermediate gear 220 is rotatably supported on the top plate 3a of the housing 3 so as to coupled with the rolling motor gear 202.

A rolling lever 221 is manually rotatably supported on the top plate 3a by means of a shaft (not shown) and a second rolling gear 222 is rotatably mounted on the rolling lever 221.

A rolling shaft 224 having a third rolling gear 223 mounted on its lower end portion is rotatably supported on a bearing member 229 provided on the top plate 3a and a third rolling gear 223 is attached to the rolling shaft 224. The third rolling gear 223 can be engaged with the second rolling gear 222 through a pinion 222a. A rolling disc member 225 is attached on the top end portion of the rolling shaft 224 with a crank pin 226 projected thereon at the position eccentric to the center of the disc member 225. The free end of the crank pin 226 is movably engaged with an elongated slot 227a of a crank lever 227 which is radially projected from a rolling cylinder rotatably inserted to the scrubbing shaft 212. In this arrangement, when the third rolling gear 223 is rotated, the crank lever 227 is reciprocally swung around the axis of the rolling shaft 230 by the crank motion of the crank pin 226 and crank lever 227. The rolling shaft 230 also penetrates the top end plate 213Y.

In operation, when the scrubbing switch 205 is pushed, the scrubbing gear 209 and the scrubbing drive gear 203 are engaged together. Upon rotation of the motor M, the rotation of the motor M is transferred to the scrubbing gear 209 which is rotated around its axis and the scrubbing shaft 212 can be reciprocally moved in the direction of the axis of the scrubbing shaft 212. Therefore when an adapter similar to the adapter shown in the first embodiment having a brush unit is mounted to the scrubbing shaft 212, the adapter can be moved in the scrubbing motion.

In case the switch 205 is pulled so that the scrubbing gear 209 is away from the scrubbing drive gear 203 and the rolling lever 221 is manually rotated so that the second rolling gear 222 is engaged with the intermediate gear 220 and the motor M is rotated, the rotation of the motor m is transferred to the third gear 223. Thus the rolling disc member 225 can rotate and the crank lever 227 is reciprocally swung and the rolling shaft 230 can also swing, thus causing the adapter attached to the rolling shaft 230 to be moved in the rolling motion.

In case the switch 205 is pushed so that the scrubbing gear 209 is engaged with the scrubbing drive gear 203 and the rolling lever 221 is rotated so that the second rolling gear 222 is engaged with the intermediate gear 220, the scrubbing shaft 212 can reciprocally move in its axial direction and the rolling shaft 230 can reciprocally swing around its axis, whereby the adapter can act either in the scrubbing motion or rolling motion.

Figure 19A:
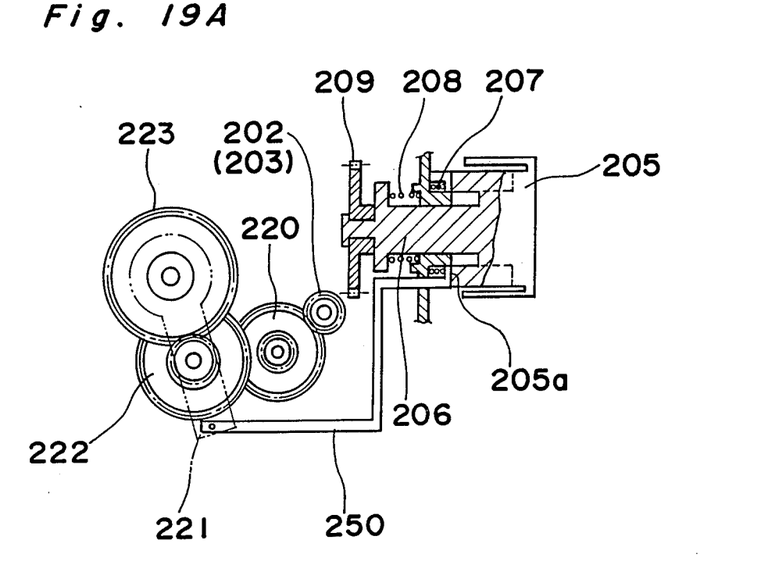
FIGS. 19A to 19D are respectively top plan view showing operation of an essential portion of the gear arrngement used in the toothbrush shown in FIG. 18
Figure 19B:
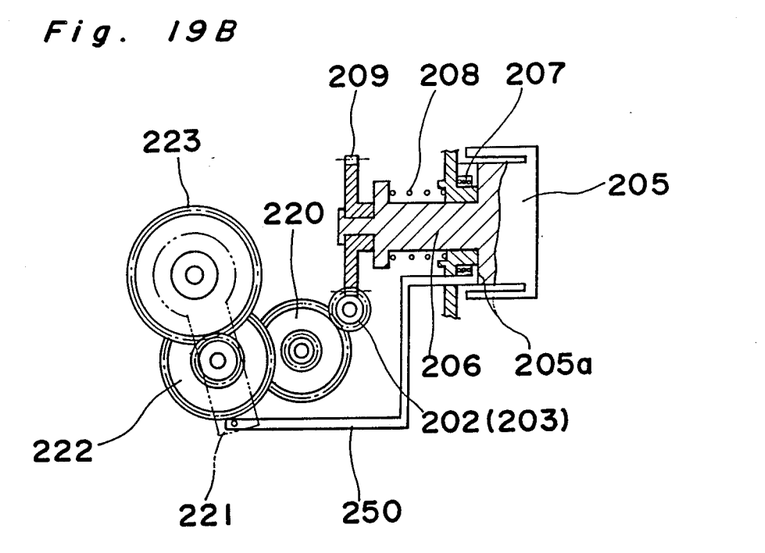
Figure 19C:
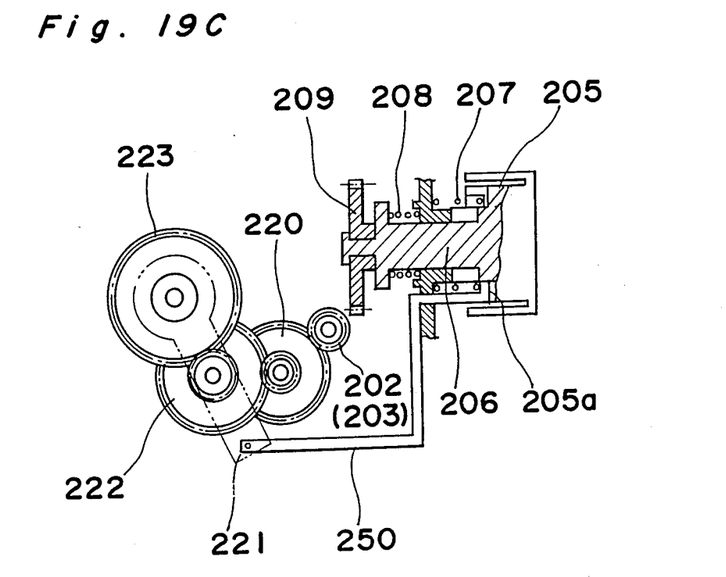
Figure 19D:
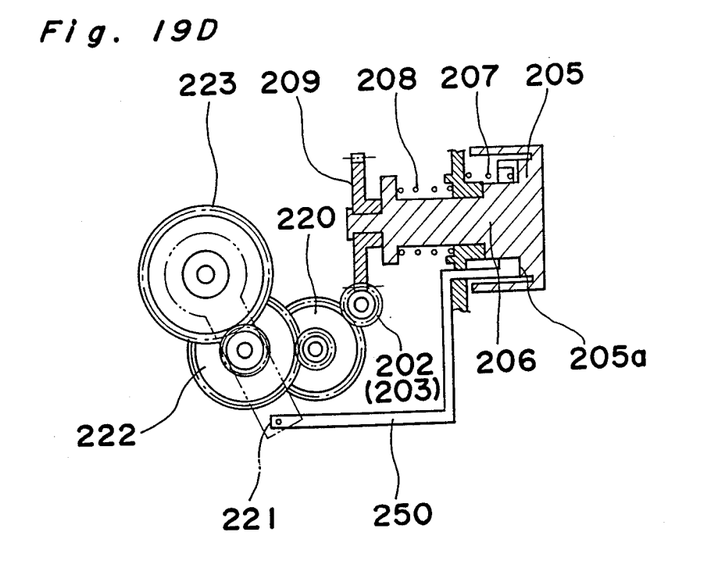

FIGS. 19A to 19D represent the states of coupling of the respective gears shown in FIG. 18. In FIGS. 19A to 19D, the switch 205 and the rolling lever 221 are coupled together through a connecting bar 250 so that the switch 205 can operate the rolling lever 221. One end of the connecting bar 250 is connected with the lever 221 and another end is slidably engaged with the inner end surface 205a of the switch 205 having the another end movably fitted to the shaft 206. Said inner end surface 205a is slanted in the circumferential direction so that rotation of the switch 205 causes the coupling bar 250 to be moved in the direction of the axis of the shaft 206 by the another end of the bar 250 being pushed by the slanted surface 205a. FIG. 19A represents that the switch 205 is pulled so that the scrubbing gear 209 and the second rolling gear 222 are disengaged from the gears 202 and 220 for stopping the scrubbing shaft 212 and rolling shaft 230. In this case, the spring 208 is half compressed and the spring 207 is fully compressed and said another end of the coupling bar is faced to the highest portion of the slanted surface 205a. In case the switch 205 is rotated so that said another end of the coupling bar is engaged with a portion of the slanted surface 205a lower than its highest portion, as shown in FIG. 19B, the scrubbing gear 209 can engage with the scrubbing drive gear 203 but the second rolling gear 222 is disengaged from the intermediate gear 220. In this case, the spring 208 is fully expanded and the spring 208 is fully compressed. In case of the state shown in FIG. 19C, by rotating the switch 205 so that said another end of the coupling bar 250 engages with the intermediate portion of the slanted surface 205a further lower than the state shown in FIG. 19B, the switch 205 is moved right with the scrubbing gear 209 disengaged from the gear 202 and the coupling bar 250 is moved right in FIG. 19C by the expansion of the spring 207 and the lever 221 is rotated so that the second rolling gear 222 engages with the intermediate gear 220 with the spring 208 half compressed and 207 half expanded, whereby only the rolling motion is performed. In case of the state shown in FIG. 19D, the switch 205 is further rotated so that said another end of the coupling bar 205 is engaged with the lowest portion of the slanted surface 205a, the switch 205 is moved left by the force of the spring 208 so as to engage with the scrubbing gear 209 with the gear 202 and the coupling bar is rotated right so that the second rolling gear 222 engages with the gear 220, whereby both the scrubbing motion and rolling motion can be performed.

Figure 20:
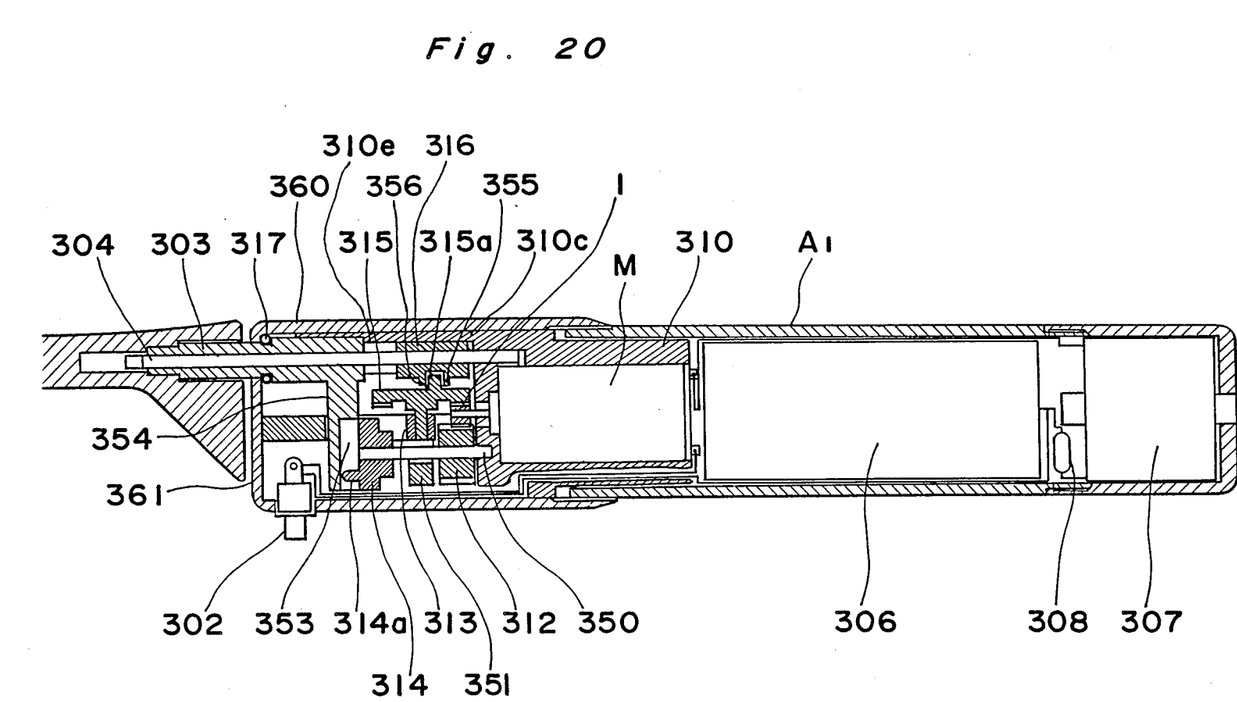
FIG. 20 is a cross sectional view of a still further embodiment of the toothbrush according to the present invention.
Figure 21:
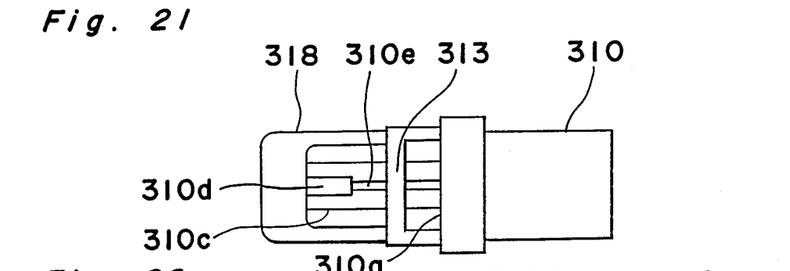
FIG. 21 is a top plan view of a housing member used in the toothbrush shown in FIG. 20.
Figure 22:
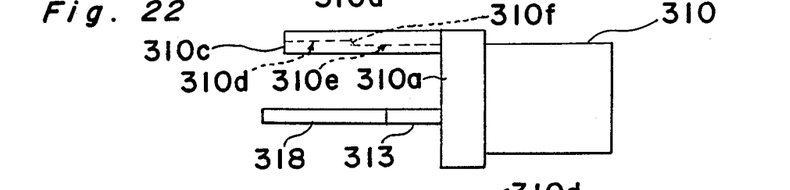
FIG. 22 is a side view of the housing member shown in FIG. 21.
Figure 23:
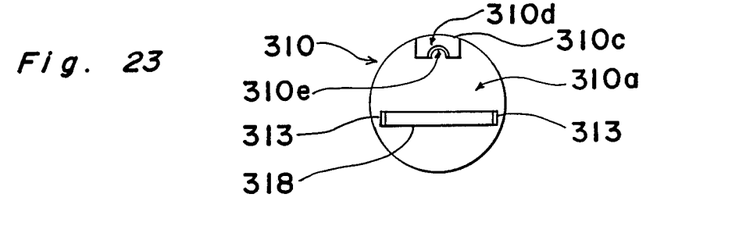
FIG. 23 is a rear view of the housing memeber shown in FIG. 21.
Figure 24:
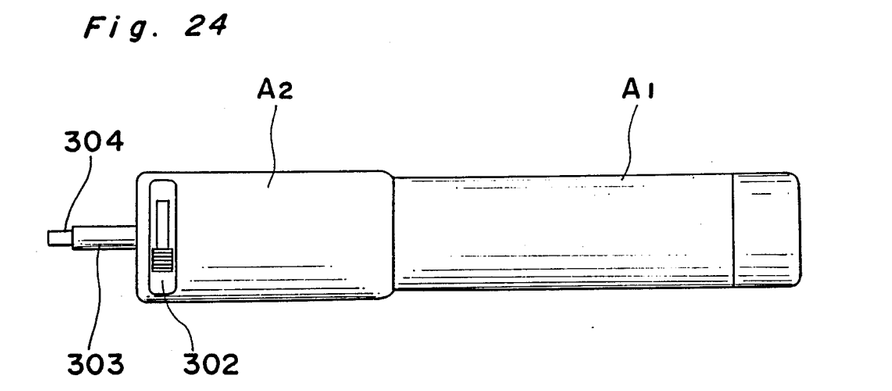
FIG. 24 is a side view of the toothbrush shown in FIG. 20.

FIG. 20 shows a fourth embodiment of the toothbrush according to the present invention in which the motor M is accommodated in a cylindrical housing 310 as shown in FIGS. 21 to 23. The rotation shaft of the motor M penetrates the end plate 310a with the motor gear 1 attached. A rolling drive gear 312 in the from of a face gear is supported by a shaft 350 so as to engage with the motor gear 1 at one end of the shaft 350 which is rotatably supported on the end plate 310a of the housing 310. The intermediate portion of the shaft 350 is rotatably supported on a bearing 351 provided in a supporting frame 313 having a generally U shaped member integrally formed with the housing 310 as shown in FIGS. 21 to 23. A rotational disc 314 having an eccentric pin 314a is supported on the other end of the shaft 350. The eccentric pin 314a is slidably coupled in an elongated slot 353 defined in a crank arm 354 radially projecting from a rolling shaft 303, so that when the rotational disc 314 is rotated, the crank arm 354 and the rolling shaft 303 are reciprocally swung around the cylindrical axis of the rolling shaft 303 by the crank motion of the crank pin 314a and the crank arm 354. The crank arm 354 is slidably supported by a guide member 318 having a generally U shape and formed integral with the housing 310. Said rolling shaft 303 is rotatably and coaxially fitted on a scrubbing shaft 304, one end of which is rotatably supported on the end plate 310a of the housing 310. Both the scrubbing shaft 304 and rolling shaft 303 project outwardly and penetrate through an end plate 361 of a cover case 360 detachably fitted to the housing 310. As shown in FIG. 20. an O ring 317 is provided at the penetrating portion of the end plate 361 for sealing.

A scrubbing gear 315 in the form of a face gear is rotatably supported on the bearing member 313 projectingly formed on the end plate 310a. The gear teeth formed on the peripheral edge of the scrubbing gear 315 are adapted to be engaged with the motor gear 1. A slider 316 having a cylindrical shape is fixedly fitted to the intermediate portion of the scrubbing shaft 304 and a crank guide member 355 is formed on the slider 316 with an elongated slot 356 formed in a direction perpendicular to the axis of the slider 316. A crank pin 315a is projected at the position eccentric to the center of the scrubbing gear on the end surface thereof and the crank pin 315a is slidably engaged in the elongated slot 356 of the crank member 355, so that when the scrubbing gear 315 rotates, the slider 316 and the scrubbing shaft 304 are reciprocally moved in a direction of the axis of the scrubbing shaft 304 by the crank motion of the crank pin 315a and the crank member 355.

Said slider 316 is slidably fitted in a round guide slot 310e defined in a guide member 310c projected from the end plate 310a. The inner part of the rolling shaft 303 is rotatably fitted in a round second slot 310d in guide member 310c having one end face of the rolling shaft 303 movably contacted with the stepped shoulder 310f to confine the rolling shaft in position. As shown in the drawings, the guide member 310c is fitted to the inner wall of the cover 360 when the cover 360 is fitted to the housing 310, so that the guide member 310c and 310d can support both of the scrubbing shaft 304 and rolling shaft 303 with high mechanical strength. A battery 306 is accommodated in the housing A so as to supply an electric power to the motor M when the switch member 302 is turned on. In the example shown in FIG. 20, a battery charger 307 is also accommodated behind the battery 306 in the housing A so as to charge the battery 306 using a commercial power source. Said switch 302 is operably provided on the cylindrical surface of the cover 360.

In operation, when the switch 302 is turned on, the motor M is driven by the battery 306 and the rotation of the motor gear 1 is transferred to the rolling drive gear 312 and scrubbing gear 315. Rotation of the rolling drive gear 312 is transferred to the rotational disc 314 and the motion of the crank pin 314a causes the rolling shaft 303 to be reciprocally swung around the axis of the rolling shaft 303. On the other hand, rotation of the motor gear 1 is transferred to the scrubbing gear 315 and the motion of the pin 315a causes the slider 316 and the scrubbing shaft 304 to be reciprocally moved in the direction of the axis of the scrubbing shaft 304. Therefore, when an adapter 330 engaging with the rolling shaft 303, is attached to the shaft 303 the adapter can reciprocally swing to move the toothbrush unit attached to the adapter in the rolling motion. When an adapter which engages only with the scrubbing shaft is attached, the adapter can reciprocally move in the direction of the axis of the scrubbing shaft 304 so that the brush unit can be moved in the scrubbing motion.

Figure 25:
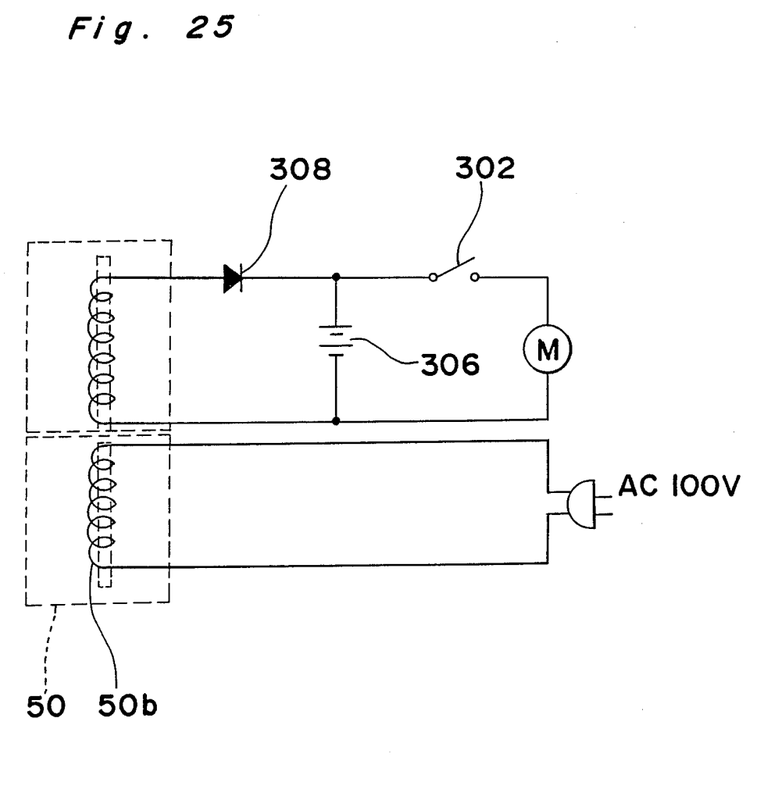
FIG. 25 is a circuit diagram used in the toothbrush shown in FIG. 20.

FIG. 25 shows a circuit diagram of a power source for use in the toothbrush arrangement mentioned above. In the circuit, a primary charging unit 50 comprises a primary transformer coil 50a which is accommodated in a stand (not shown) having a recess for detachably accommodating the end portion of the housing A1. A secondary coil 307 is installed in the end portion of the housing A1 so that the secondary coil is electromagnetically coupled with the primary coil 50b. The output AC power of the secondary coil is applied to a diode 508 which is connected to the battery 306 which is connected to the motor M through the switch 302. In this arrangement, by turning on the switch 302, the motor M can be driven by the power of the battery 306. When the housing of the toothbrush is inserted in the recess of the stand with the switch 302 turned off and the commercial AC power is supplied to the primary coil 50a, the secondary coil 307 induces AC power and the AC power is rectified into DC power by the diode 308 and the battery 306 is charged.

What is claimed is:

1. A motor driven toothbrush comprising a housing having an end plate formed on one end portion of the housing, an electric motor accommodated in the housing with the motor shaft projected outward of the housing through the end plate, a scrubbing shaft supported on a standard secured to the end plate of the housing for moving in a direction of the axis of the scrubbing shaft, a rolling shaft coaxially fitted to the scrubbing shaft for moving around the axis of the rolling shaft, first drive means driven by the rotation of the electric motor for driving said scrubbing shaft reciprocally in the axial direction, second drive means driven by the rotation of the electric motor for swinging said rolling shaft reciprocally around the axis of the rolling shaft, and adapter means having a toothbrush unit and being detachably mounted to the rolling shaft and/or the scrubbing shaft.

2. The motor driven toothbrush according to claim 1, wherein said first drive means comprise a plurality of first gears each being rotated in a plane parallel to the axis of the scrubbing shaft and a crank pin provided on one of the gears at a position eccentric to the center of said one of the gears and a crank member having a guide slot slidably engaged with said crank pin to reciprocally move the crank member and the scrubbing shaft in the axial direction and said second drive menas comprise a plurality of second gears each being rotated in a plane perpendicular to the axial direction of the rolling shaft, a cylindrical rolling crank member rotatably supported on a frame member secured to the end plate coaxial to the rolling shaft, a crank lever radially projected from the cylindrical surface of the rolling crank member and a crank pin disposed relative to any one of the second gears eccentric from the center of said one of the second gears and being slidably engaged with the crank lever so as to reciprocally to rotate the rolling crank member and the rolling shaft.

3. The motor driven toothbrush according to claim 1, wherein said first drive means includes a scrubbing gear rotating in a plane parallel to the axis of the scrubbing shaft, a crank pin disposed on said scrubbing gear eccentric from the center thereof and a crank lever having one end rotatably coupled to the crank pin and another end coupled to the end portion of the scrubbing shaft.

4. The motor driven toothbrush according to claim 1, wherein said first drive member comprises a plurality of gears each being rotated in a plane perpendicular to the axis of the scrubbing shaft, a cam member having a cylindrical drum with one end surface formed in a wave shape and formed on one of the gears and a cam follower attached to the scrubbing shaft and being movable along the wave shape of the cam member.

5. The motor driven toothbrush according to claim 4, wherein said cam follower comprises a disc fixed to the scrubbing shaft, pin projected from the disc so as to slidably contact to the end surface of the cam member.

6. The motor drive toothbrush according to claim 1, wherein said first drive means comprises a gear rotatably supported on a frame projected from said end plate for rotation in a plane parallel to the axis of the scrubbing shaft and a crank pin projected from said gear at a position eccentric from the center of the gear and a slider secured to the scrubbing shaft and having guide member with a slot extending perpendicular to the axis of the scrubbing shaft, said pin being slidably engaged in said slot of the guide member and said second drive means comprises a rotation disc being rotatable in a plane perpendicular to the axis of the rolling shaft and having a crank pin disposed at a position eccentric from the center of the rotation disc and a crank member radially projected from the rolling shaft with an elongated slot, said crank pin being slidably engaged in said elongated slot.

7. A motor driven toothbrush comprising a housing having an end plate formed on one end portion of the housing, an electric motor accommodated in the housing with the motor shaft projected outward of the housing through the end plate, a scrubbing shaft supported on standard secured to the end plate of the housing for moving in a direction of the axis of the scrubbing shaft, a rolling shaft coaxially fitted to the scrubbing shaft for moving around the axis of the rolling shaft, first drive means driven by the rotation of the electric motor for driving said scrubbing shaft reciprocally in the axial direction, second drive means driven by the rotation of the electric motor for swinging said rolling shaft reciprocally around the axis of the rolling shaft, and means for selecting which of the scrubbing shaft and rolling shaft is driven.

8. The motor driven toothbrush according to claim 7, wherein said selecting means comprises means for moving said first drive means and second drive means so as to detachably couple said shafts to the motor.

* * * * *